United States Patent [19]

Papp, Jr.

[11] Patent Number: 4,935,019
[45] Date of Patent: Jun. 19, 1990

[54] RADIOPAQUE POLYMERIC COMPOSITION

[75] Inventor: Stephen Papp, Jr., Edison, N.J.

[73] Assignee: Johnson & Johnson Medical, Inc., Arlington, Tex.

[21] Appl. No.: 189,078

[22] Filed: May 2, 1988

Related U.S. Application Data

[63] Continuation-in-part of Ser. No. 944,135, Dec. 22, 1986.

[51] Int. Cl.$^5$ .................... A61F 13/16; A61F 13/18; A61F 13/20
[52] U.S. Cl. .................................. 604/362; 604/370; 128/156; 424/4; 523/117
[58] Field of Search ............... 604/362, 370; 128/156, 128/653, 654, 656; 424/4; 523/117; 260/998.11

[56] References Cited

U.S. PATENT DOCUMENTS

| | | | |
|---|---|---|---|
| 2,996,433 | 8/1961 | Hoppe et al. | 424/4 |
| 3,911,922 | 10/1975 | Kliger | 604/362 |
| 4,639,253 | 1/1987 | Dyer et al. | 604/362 |
| 4,718,897 | 1/1988 | Elves | 604/362 |

Primary Examiner—Stephen C. Pellegrino
Assistant Examiner—Michael Rafa

[57] ABSTRACT

A radiopaque, polymeric composition suitable for printing onto surgical fabrics to provide an X-ray detectable marker is obtained by dispersing a heavy metal salt such as barium sulfate in a liquid polymer carrier. The barium sulfate has an average particle size greater than about 5 microns and is present in an amount of from about 15 to 90% by weight of total solids of said composition.

16 Claims, 4 Drawing Sheets

FIG-3
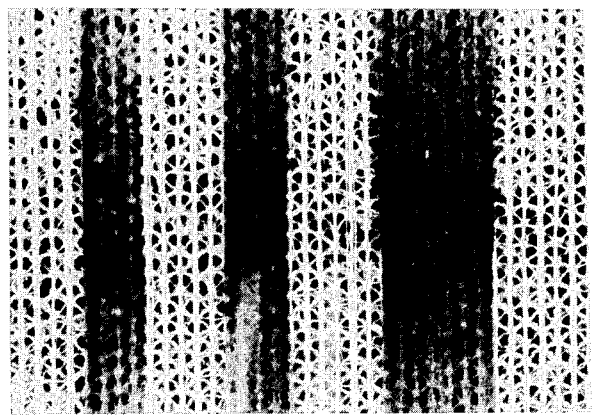
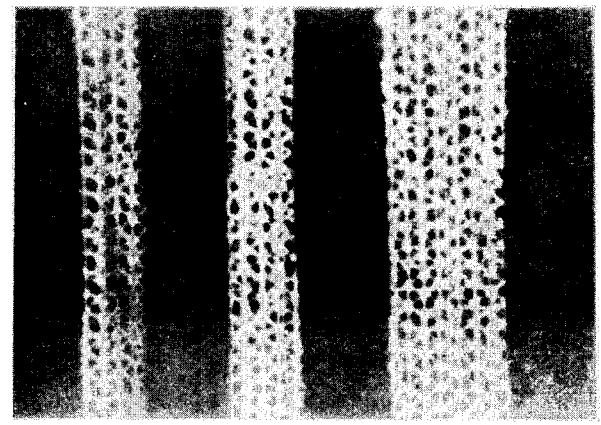

RADIOPAQUE POLYMERIC COMPOSITION

CROSS REFERENCE TO RELATED APPLICATIONS

This application is a continuation-in-part of copending application Ser. No. 944,135 filed Dec. 22, 1986.

FIELD OF THE INVENTION

This invention relates to X-ray detectable fabrics and, more particularly, to a radiopaque polymeric composition which may be applied to the surface of the fabric by printing or extrusion to form an integral component of the sponge fabric.

BACKGROUND OF THE INVENTION

Various absorbent fabric materials are used in surgical procedures for packing, wiping, and cleansing in or around the operating site. Typical products include surgical sponges such as 4×4 inch folded surgical gauze of nonwoven fabric, and woven, nonwoven and knitted laparotomy pads. Although standard operating room procedures require all materials brought into the operating area to be accounted for upon completion of the procedure, an occasional sponge may inadvertently be left in the patient. It is accordingly common practice in the medical field to include a radiopaque marker on all surgical sponges so that the presence or absence of a sponge in a patient experiencing difficulty after an operation can be determined by X-ray examination rather than by reoperating on the patient. A common X-ray detectable marker used in conjunction with surgical sponges is a polymeric filament or ribbon loaded with an X-ray opaque filler material such as barium sulfate.

Suitable polymeric materials include polyisobutylene, polyvinyl chloride and copolymers of vinyl acetate and vinyl chloride. Such X-ray detectable elements have been incorporated into sponge material by a variety of techniques. In the case of gauze swabs, a filament has been interwoven into the fabric of the gauze or fused to the surface of the fabric and folded into the sponge construction. In the case of laparotomy pads, an X-ray detectable ribbon has been enclosed in a seam stitched along one end of the pad, or an X-ray detectable filament has been incorporated into the woven handle strap of the pad or into the body of the pad fabric. In the case of nonwoven fabric sponges, the filament has been either heat fused onto the surface of the fabric or incorporated into the fabric by introducing the radiopaque element during the fabric manufacturing process.

In all cases, the X-ray detectable element has been preformed as a ribbon, yarn or monofilament, and it has been essential to securely attach the element to the sponge fabric since if the element is separated from the fabric during use, not only is the fabric no longer visible by X-ray, but the separated element is easily lost in the surgical field. For manufacturing considerations, it is desirable that the X-ray detectable marker be secured to the sponge in a continuous and reliable manner with a minimum of labor. A final consideration is that the X-ray detectable marker be easily identified in an X-ray image.

It is accordingly an object of the present invention to provide an improved X-ray detectable marker on a surgical sponge. It is a further object of this invention to provide a surgical sponge having a distinctive and easily detected radiopaque marker. It is a yet further object to provide a radiopaque polymeric composition which may be applied to a fabric in a rapid, continuous and economical manner. These and other objects of the present invention will be apparent from the ensuing description and claims.

SUMMARY OF THE INVENTION

A surgical sponge in accordance with the present invention comprises a fabric and a radiopaque marker bonded to said fabric in a visually distinctive pattern. The radiopaque marker is applied to the fabric by extruding or printing a radiopaque polymeric suspension or melt onto the surface of the fabric in such a way that the surface fibers of the substrate fabric are encapsulated. Upon heat-setting, curing or coalescing, the radiopaque material is securely bound to the fabric so that it becomes an integral part of the fabric and cannot be readily removed. Emulsion polymers such as plastisols and latexes which are soft, rubbery materials even when heavily loaded with barium sulfate or other radiopaque salt are well suited for use in the present invention.

The pattern of the X-ray detectable marker is determined by the structure of the underlying fabric and the nature of the application means. The marker may be applied to the fabric in a continuous process at a high rate of speed by printing with a gravure roll. Suitable compositions for the marker comprise biocompatible polymers containing an effective amount of a radiopaque filler such as barium sulfate and having a viscosity suitable for printing or other application means. The radiopaque filler preferably has an average particle size of 5 microns or greater and is present in an amount of from about 15 to 90 parts by weight of solids.

DESCRIPTION OF THE DRAWINGS

FIG. 3 is a photograph of a nonwoven fabric having a radiopaque marker applied to the surface thereof.

FIG. 4 is a print of an X-ray image of the fabric of FIG. 3 illustrating the pattern of the X-ray marker.

DESCRIPTION OF THE INVENTION

Figure 1:
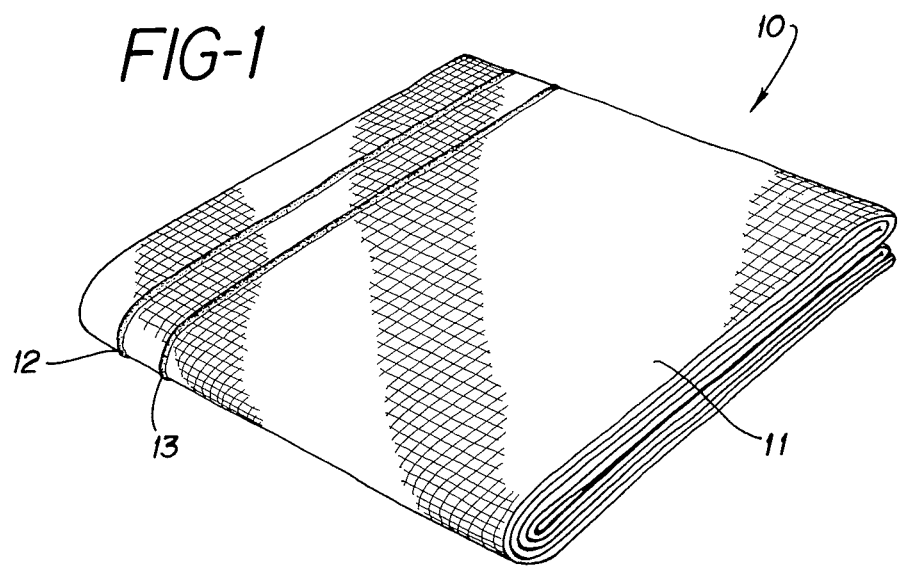
FIG. 1 is a view in perspective of a folded surgical sponge having an X-ray detectable marker in accordance with the present invention.

The present invention consists of applying a polymeric material comprising a polymeric carrier and from about 15 to about 90 percent by weight of solids of a heavy metal radiopaque, salt such as barium sulfate onto the surface of surgical sponge fabrics. The polymeric material may be applied as a hot melt extrusion, or by printing or cold extruding a latex emulsion or a plastisol onto the surface of the fabric in a continuous or intermittent pattern. Upon heat-setting, curing or coalescing, the upper layer of fibers of the underlying fabric are encapsulated by the radiopaque material so that the marker is securely bound to the surface of the fabric and will not separate during normal handling or use.

The radiopaque marker may be applied to the fabric in a distinctive pattern which is readily identified in an X-ray image. In the case of those fabrics having an open structure such as woven gauze and certain nonwoven fabrics, the radiopaque material may be applied to the fabric in such a way as to preserve the open spaces in the fabric whereupon the fabric structure itself becomes the distinctive pattern of the X-ray marker.

In the case of fabrics having no distinguishable pattern such as closely knit or tightly-woven fabrics or nonapertured nonwoven fabrics, it is preferable to apply the radiopaque material to the surface of the fabric in a predetermined pattern which is controlled by the configuration of the printing roll or other application means. Latex emulsions and plastisol formulations may be applied to the fabric by padding, gravure printing, screen printing, or other convenient method.

Patterned nonwoven fabrics useful in the practice of the present invention may be prepared according to conventional hydraulic entanglement methods. In brief, these methods consist of providing a fibrous web of randomly oriented staple length fibers, positioning the web on a patterned, apertured belt, and subjecting the web to a plurality of high pressure hydraulic jets to entangle the fibers into a pattern conforming to that of the supporting belt. The entangled fibers are thereupon separated from the belt and dried on hot drums to produce a patterned nonwoven fabric. This method of manufacturing is described in detail in U.S. Pat. Nos. 3,068,547; 3,129,466; 3,485,706; 3,494,821; and 3,681,184 and is well known to those skilled in the art.

The nonwoven fabric may comprise any suitable combination of natural and/or synthetic textile materials including cotton, rayon, acrylics, polyester and nylon. A particularly preferred fiber composition is a blend of 70% rayon (1.5 denier, approximately 3 cm staple length) and 30% polyester (1.5 denier, approximately 3 cm staple length). The staple fibers are blended and converted to a fibrous web on conventional textile processing equipment such as a Rando-Webber which produces a web having random fiber orientation. The nonwoven fabric preferably has a dry weight of from about 1.0 to 3.0 ozs per square yard (30 to 100 g/m$^2$), with the lighter weights limited by the processability of the fibrous web and the heavier weights limited by the desired utility and construction of the sponge or swab, although higher weights may be preferred for some product applications such as laparotomy pads.

The radiopaque composition is preferably dyed or pigmented blue or other suitable color which contrasts sharply with blood. The color permits ready identification of the X-ray detectable element in the sponge, facilitates sponge counting in the operating room and further helps locate the sponge when saturated with blood during use. As a characteristic of the sponges of the present invention, the radiopaque material may be applied primarily to one surface of the fabric, and is consequently visually more apparent from that side. This increased visibility may be capitalized on when folding the sponge by placing the radiopaque material to the outside of the sponge.

Figure 2:
FIG. 2 is a print of an X-ray image of a double thickness of a nonwoven fabric having two narrow X-ray detectable bands printed thereon.

Turning now to FIG. 1 there is illustrated a surgical sponge, indicated generally by the numeral 10, which consists of folded fabric 11 having a radiopaque marker consisting of a pair of lines 12 and 13. The radiopaque marker lines are continuous over the length of the folded sponge and applied to the fabric during manufacture by, for example, printing a radiopaque plastisol directly onto the surface of the fabric. While lines 12 and 13 appear generally as two continuous lines of uniform width and depth, closer inspection reveals that the lines conform to the open pattern of the fabric and have a variable thickness on the surface of the fabric. The pattern of the radiopaque material on the fabric of the sponge results in the formation of a distinctive X-ray image of the radiopaque marker. FIG. 2 is a print of the X-ray image of a double thickness of a fabric having two narrow X-ray detectable bands printed thereon. While the X-ray pattern is created entirely by the pattern of the underlying fabric, the fabric pattern itself is not apparent from the X-ray image due to the narrow width of the radiopaque lines.

Figure 5:
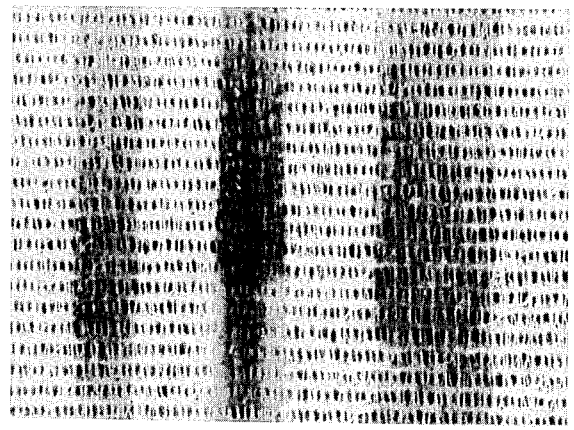
FIG. 5 is a photograph of another nonwoven fabric having a radiopaque marker applied to the surface thereof.
Figure 6:
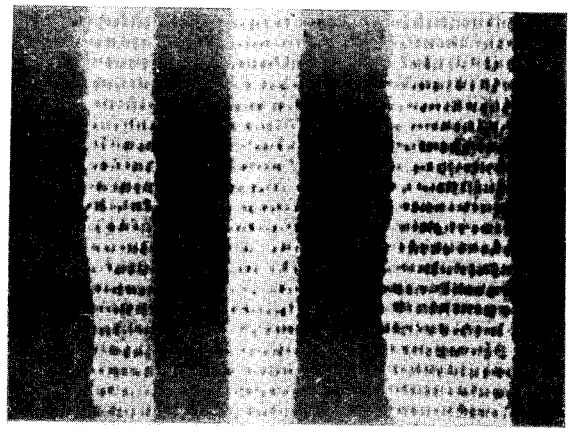
FIG. 6 is a print of an X-ray image of the fabric of FIG. 5 illustrating the pattern of the X-ray marker.

FIG. 3 is a photograph of an open patterned nonwoven fabric which is characterized by a series of small, widely-spaced fiber masses interconnected by radial threads in what is commonly referred to as a "rosebud" pattern. A radiopaque material applied uniformly to the fabric over a width of from about 1 to 2 cm, appearing as dark bands in FIG. 3, encompasses a sufficient area of fabric to make the actual pattern of the fabric visible in the X-ray image as illustrated in FIG. 4. Where such a wide band of radiopaque material is applied to the fabric, it will usually be sufficient to apply the material in a discontinuous line so that one or two bands of material appear in each sponge. For example, if the length of the fabric comprising each folded sponge is 0.5 m, it would be sufficient to apply the radiopaque material in bands of 2 cm wide by 10 cm long at a frequency of four bands per meter of fabric, thus assuring that each sponge would include two radiopaque markers, at least one of which would be a continuous 10 cm length. FIG. 5 is a photograph of another nonwoven fabric having a radiopaque marker applied to the surface thereof. The X-ray image of the fabric as illustrated in FIG. 6 clearly shows the pattern of the fabric to be different than that of FIG. 4.

Figure 7:
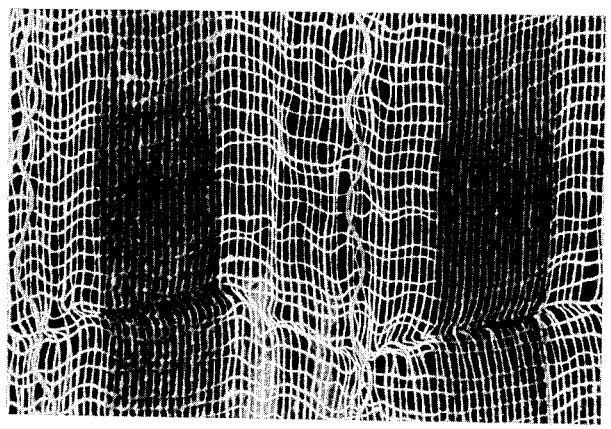
FIG. 7 is a photograph of a surgical gauze having a radiopaque marker applied to the surface thereof and also containing a conventional X-ray detectable monofilament.
Figure 8:
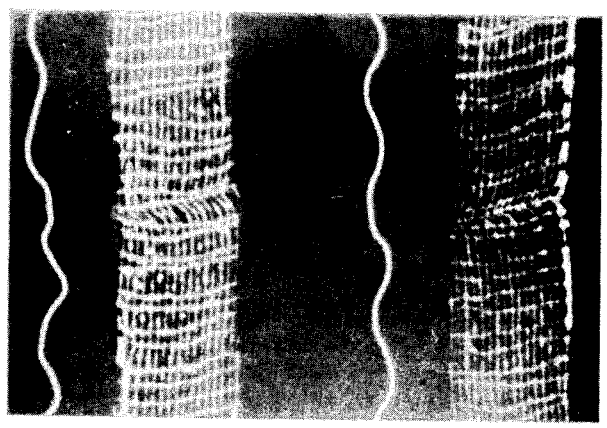
FIG. 8 is a print of an X-ray image of the fabric of FIG. 7.

FIG. 7 illustrates a conventional 20×8 woven surgical gauze printed with a band of radiopaque plastisol material which appears as the dark bands in the photograph of FIG. 7. The radiopaque material uniformly coats each yarn of the gauze within the area of the coating and the pattern of the gauze is readily identified in an X-ray image of the fabric as illustrated in FIG. 8. FIGS. 7 and 8 also include a conventional monofilament marker which is clearly visible as the wavy line in the X-ray image of FIG. 8, and less evident in the photograph of the fabric of FIG. 7. It should also be noted that while the photograph and the X-ray are of the same fabric, the displayed areas are not precisely the same.

As illustrated in FIGS. 1–8, the radiopaque material may be applied to an open mesh fabric over an area sufficient to reveal the actual pattern of the underlying fabric in an X-ray image, or over an area which is too narrow to disclose the repeating pattern of the fabric, but nevertheless displays a distinctive pattern of its own in an X-ray image as a result of the underlying fabric pattern.

In the case of closely knit or woven fabric, the radiopaque material is applied in a predetermined pattern controlled by the application means. For example, a plastisol may be applied to the fabric by screen printing or by gravure system in a continuous line or in discontinuous bands and in any desirable pattern. An infinite variety of patterns is, of course, possible and may be utilized in the practice of the present invention. One desirable pattern would be in the name or initials of the supplier of the surgical product and perhaps the order number of the product, which would not only provide X-ray detectability but also indicate the source of the product to the surgeon during the operating procedure. Since the surgical sponges are usually wadded up during use, it is unlikely that this information would be fully legible in an actual X-ray image, but even a single letter of the alphabet would be distinctive and easily recognized as a foreign object in an X-ray following a surgical procedure.

The method of the present invention is further illustrated in the following examples where all parts and percentages are by weight unless otherwise indicated.

EXAMPLE 1

A plastisol printing composition containing 61.5% $BaSO_4$ is prepared from polyvinyl chloride resin according to the following formulation:
100 parts Geon 125-A PVC resin
100 parts Dioctyl phthalate plasticizer
328 parts $BaSO_4$
5 parts blue pigment Geon TM 125-A PVC resin is a low molecular weight, low viscosity polyvinylchloride powder available from B.F. Goodrich, Avon Lake, Ohio. The $BaSO_4$ is suitably No. 1 Barytes TM HP available from Pfizer, Inc., Easton, Pa. The blue pigment is suitably Ultramarine Blue available from Sun Chemical Co., Cincinnati, Ohio. The PVC resin is sifted with stirring into the dioctyl phthalate plasticizer containing the blue dye, followed by addition of the $BaSO_4$. The resulting composition contains about 81% total solids and has a Brookfield viscosity of about 20,000 cps at room temperature which is suitable for printing. Desirable viscosities for printing are generally in the range of 2,000 to 20,000 cps although higher or lower viscosities may be utilized in some applications. Upon removal of volatiles, the resulting polymeric composition contains about 76% $BaSO_4$.

EXAMPLE 2

An emulsion latex printing composition containing 67.2% $BaSO_4$ is prepared according to the following formulation:
25 parts water
10 parts blue pigment
2 parts antifoam
4 parts rheology modifier
3 parts ammonia (28%)
200 parts Rhoplex K-3 (48%)
501 parts $BaSO_4$ The latex printing composition containing about 81% total solids is prepared by first combining the water, ammonia, antifoam, rheology modifier, pigment and Rhoplex TM K-3, then slowly adding the $BaSO_4$ with stirring. The ammonia functions to increase the pH to about 8, the antifoam may be Colloids 999 available from Colloids, Inc., Newark, NJ, and the rheology modifier may be a poly (ethylene oxide) such as Polyox TM available from Union Carbide, Danbury, Conn. Rhoplex K-3, is a 46% aqueous acrylic emulsion available from Rohm & Haas, Philadelphia, Pa. After application to the fabric and removal of volatiles, the $BaSO_4$ content in the resulting polymeric composition is approximately 80 percent.

EXAMPLE 3

A high loading acrylic latex emulsion containing 68.2% $BaSO_4$ is prepared according to the following formulation:
100 parts Rohm & Haas 7R-934
100 parts National Starch 4401
3 parts ammonium hydroxide (28%)
3 parts antifoam
4 parts blue pigment
450 parts $BaSO_4$ The acrylic emulsion containing about 83% solids is prepared by combining and blending the components as described in Example 2. In this example, the antifoam was Dow Corning Y-30 silicone emulsion, the blue pigment was dry, cosmetic grade Sun Chemical Ultramarine Lake Blue, and the $BaSO_4$ was Pfizer Barytes #1 HP. Rohm & Haas 7R-934 is a milky white aqueous emulsion containing 45% acrylic polymer. National Starch 4401 is a vinyl acetate/acrylic copolymer emulsion of 49% solids. After removing the volatiles from the formulated mixture, the resulting polymeric composition contains 17.3% latex, 82% $BaSO_4$, and 0.7% pigment.

The radiopaque polymeric composition with $BaSo_4$ is naturally white, but may be pigmented blue or other color for enhanced visibility, or left uncolored except for some indication of its presence such as a thin blue line printed onto the marker after curing. A wide, unpigmented band of radiopaque material with a narrow blue line or the logo of the manufacturer printed thereon, may be more aesthetically pleasing to the surgeon and still provide all the advantages of a wide, X-ray detectable marker as described herein.

The plastisol or latex printing composition is applied to the surgical fabric using conventional printing equipment and techniques as, for example, by gravure rolls. The printed fabric is passed through a heating station to Polymerize the resin and remove volatile components. The resulting polymeric deposit is securely adhered to the underlying fabric and typically comprises from about 60-90% $BaSO_4$ solids in the resin binder. We have found that at least 10% resin binder is desirable to assure the integrity of the polymeric mass and its adhesion to the fabric. The $BaSO_4$ used in the printing formulations of the present invention preferably has an average particle size of at least 5 microns, and most preferably 10 microns or greater, in order to obtain printing compositions having the desired flow characteristics when containing up to about 70% $BaSO_4$ solids. We have found that when the average particle size is substantially less than 5 microns, as for example 2 microns, formulations containing such high levels of $BaSO_4$ solids are essentially dry mixes not suitable for application to fabric by conventional printing means. In the case of the No. 1 Barytes HP used in the preceding examples, the average particle size is about 10 microns with 75 percent of the particles being 5 microns or greater.

We have also found that the X-ray detectability of a cured latex or plastisol containing from 60 to 70 percent barium sulfate compares favorably with that of a conventional monofilament marker which usually contains about 60 percent barium sulfate. Moreover, the X-ray visibility of the radiopaque material is greater in the case of the present invention, since if the X-ray is taken in plan view, the pattern of the marker stands out while if the X-ray is taken in side view, the effective thickness of the marker is increased and the brightness of the marker in the X-ray image is enhanced.

The fabric may be printed on one or both sides with the radiopaque material and superimposed printing on both sides has the advantage of presenting thinner layers with greater surface area to speed drying or curing of the radiopaque material. Wide lengths of fabric may be printed with parallel bands of radiopaque material spaced to conform to the desired final width of the sponge so that the fabric may be slit within the bands. The radiopaque material thereby performs the dual function of stabilizing the cut edges of the fabric against loose yarns or linting, while at the same time imparting X-ray detectability to the fabric.

These and other variations of the present invention which is directed broadly to printing polymeric compositions onto fabrics for use as surgical sponges will be apparent to those skilled in the art. The fabrics and polymeric compositions as described herein are for the purposes of illustration only and not limiting of the present invention.

We claim:

1. A radiopaque, polymeric composition comprising a fluid polymeric emulsion and from about 15 to 90% by weight of solids of a heavy metal radiopaque salt having an average particle size of more than about 5 microns, said radiopaque composition having a Brookfield viscosity of less than about 20,000 cps at room temperature whereby by said composition is suitable for printing onto a fabric surface by gravure or screen printing.

2. The composition of claim 1 wherein said heavy metal radiopaque salt is barium sulfate.

3. The composition of claim 2 wherein said barium sulfate has an average particle size of about 10 microns with 75% of the particles being 5 microns or greater.

4. The composition of claim 3 wherein said barium sulfate comprises from about 60 to 90% by weight of solids of said composition.

5. The composition of claim 4 wherein said viscosity is from about 2,000 to 20,000 cps.

6. The composition of claim 1 wherein said liquid polymeric emulsion is an aqueous acrylic latex emulsion.

7. The composition of claim 6 wherein said acrylic latex comprises a vinyl acetate/acrylic copolymer.

8. The composition of claim 1 wherein said liquid polymeric emulsion is a PVC plastisol.

9. A radiopaque, polymeric composition comprising an aqueous emulsion of an acrylic latex carrier and from about 15 to 90% by weight of solids of a heavy metal radiopaque salt having an average particle size greater than about 5 microns, said radiopaque composition having a Brookfield viscosity of less than about 20,000 cps whereby said composition is suitable for printing onto a fabric surface by gravure or screen printing.

10. The composition of claim 9 wherein said heavy metal radiopaque salt is barium sulfate.

11. The composition of claim 10 wherein said barium sulfate has an average particle size of about 10 microns with 75% of said particles being 5 microns or greater.

12. The composition of claim 11 wherein said barium sulfate comprises from 60 to 90% by weight of solids of said composition.

13. A radiopaque, polymeric composition comprising an aqueous emulsion of an plastisol carrier and from about 15 to 90% by weight of solids of a heavy metal radiopaque salt having an average particle size greater than about 5 microns, said radiopaque composition having a Brookfield viscosity of less than about 20,000 cps whereby said composition is suitable for printing onto a fabric surface by gravure or screen printing.

14. The composition of claim 13 wherein said heavy metal radiopaque salt is barium sulfate.

15. The composition of claim 14 wherein said barium sulfide has an average particle size of about 10 microns with 75% of said particles being 5 microns or greater.

16. The composition of claim 15 wherein said barium sulfate comprises from 60 to 90% by weight of solids of said composition.

* * * * *

UNITED STATES PATENT AND TRADEMARK OFFICE
CERTIFICATE OF CORRECTION

PATENT NO. : 4,935,019
DATED : June 19, 1990
INVENTOR(S) : Stephen Papp, Jr.

It is certified that error appears in the above-identified patent and that said Letters Patent is hereby corrected as shown below:

In claim 15, column 8, lines 42-43 "barium sulfide" should be --barium sulfate--.

Signed and Sealed this

Twenty-first Day of July, 1992

Attest:

DOUGLAS B. COMER

*Attesting Officer*  *Acting Commissioner of Patents and Trademarks*